(12) United States Patent
Motellier et al.

(10) Patent No.: US 9,833,750 B2
(45) Date of Patent: Dec. 5, 2017

(54) METHOD FOR PRODUCING A FILTER INTENDED TO FILTER NANOPARTICLES, OBTAINED FILTER AND ASSOCIATED METHOD FOR THE COLLECTION AND QUANTITATIVE ANALYSIS OF NANOPARTICLES

(71) Applicant: COMMISSARIAT A L'ENERGIE ATOMIQUE ET AUX ENERGIES ALTERNATIVES, Paris (FR)

(72) Inventors: Sylvie Motellier, Saint-Laurent-du-Pont (FR); Simon Clavaguera, Grenoble (FR); Korian Lhaute, Poisat (FR); Olivier Poncelet, Grenoble (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 224 days.

(21) Appl. No.: 14/759,339

(22) PCT Filed: Dec. 24, 2013

(86) PCT No.: PCT/IB2013/061315
§ 371 (c)(1),
(2) Date: Jul. 6, 2015

(87) PCT Pub. No.: WO2014/106797
PCT Pub. Date: Jul. 10, 2014

(65) Prior Publication Data
US 2015/0336059 A1    Nov. 26, 2015

(30) Foreign Application Priority Data
Jan. 3, 2013  (FR) ..................... 13 50033

(51) Int. Cl.
*B01D 53/22*    (2006.01)
*B01D 71/50*    (2006.01)
(Continued)

(52) U.S. Cl.
CPC ........... *B01D 71/50* (2013.01); *B01D 53/228* (2013.01); *B01D 63/087* (2013.01);
(Continued)

(58) Field of Classification Search
CPC ......... G01N 23/223; G01N 2015/0038; G01N 2223/076; G01N 2223/635;
(Continued)

(56) References Cited

U.S. PATENT DOCUMENTS 5,276,106 A *  1/1994  Portelli ..................... C08J 5/24
                                                  525/423
5,338,334 A *  8/1994  Zhen ........................ B01J 23/75
                                                  501/84

(Continued)

FOREIGN PATENT DOCUMENTS

FR    12 55785 A      3/1961
JP    2004-275986 A  10/2004
JP    2007-054693 A   3/2007

OTHER PUBLICATIONS

Zhang et al., "Preparation of supported metallic nanoparticles using supercritical fluids: a review", Journal of Supercritical Fluids, vol. 38, 2006, pp. 252-267.

(Continued)

*Primary Examiner* — Anthony Shumate
(74) *Attorney, Agent, or Firm* — Oliff PLC

(57) ABSTRACT

The present invention relates to a method for impregnating a filter having pores suitable for retaining particles within them that may be present in a flow of air suitable for passing through the filter, according to which the filter made up of (Continued)

a polymer membrane is impregnated with one or more organometallic salts by applying a treatment using supercritical $CO_2$, the metal M of each salt being chosen from among the group of rare earths, yttrium, scandium, chromium, or a combination thereof. The invention also relates to the obtained filter and an associated method for the collection and quantitative analysis of nanoparticles.

24 Claims, 4 Drawing Sheets

(51) Int. Cl.
- *B01D 67/00* (2006.01)
- *B01D 69/12* (2006.01)
- *B01D 71/48* (2006.01)
- *B01D 63/08* (2006.01)
- *B01D 69/14* (2006.01)
- *G01N 23/223* (2006.01)
- *G01N 15/00* (2006.01)

(52) U.S. Cl.
CPC ..... *B01D 67/0079* (2013.01); *B01D 67/0088* (2013.01); *B01D 69/12* (2013.01); *B01D 69/148* (2013.01); *B01D 71/48* (2013.01); *G01N 23/223* (2013.01); *B01D 2053/221* (2013.01); *B01D 2323/18* (2013.01); *B01D 2323/225* (2013.01); *B01D 2323/46* (2013.01); *G01N 2015/0038* (2013.01); *G01N 2223/076* (2013.01); *G01N 2223/635* (2013.01)

(58) Field of Classification Search
CPC ............ B01D 2323/46; B01D 67/0079; B01D 2323/225; B01D 71/48; B01D 63/087; B01D 71/50; B01D 2323/18; B01D 2053/221; B01D 53/228; B01D 69/12; B01D 69/148; B01D 67/0088; B01D 53/22

See application file for complete search history.

(56) References Cited

U.S. PATENT DOCUMENTS

| | | | | |
|---|---|---|---|---|
| 5,599,383 A * | 2/1997 | Dyer | ...................... | B01D 53/22 96/10 |
| 5,750,303 A * | 5/1998 | Inaba | ................. | G03G 9/08755 430/108.4 |
| 6,299,668 B1 * | 10/2001 | Penth | ................. | B01D 46/0056 204/157.3 |
| 6,703,112 B1 * | 3/2004 | Farooq | ................... | B41M 5/508 347/105 |
| 9,393,673 B2 * | 7/2016 | Eilers | | |
| 2003/0143345 A1 * | 7/2003 | Satou | ................... | B41M 5/5218 428/32.1 |
| 2004/0019143 A1 * | 1/2004 | Koloski | ............... | C08F 283/00 524/434 |
| 2004/0067366 A1 * | 4/2004 | Gorczyca | ........... | C08G 59/4284 428/413 |
| 2004/0115370 A1 * | 6/2004 | Funakoshi | ............... | B41M 5/52 428/32.1 |
| 2004/0183055 A1 * | 9/2004 | Chartier | ............. | B01D 39/2027 252/500 |
| 2005/0014901 A1 * | 1/2005 | Osae | ..................... | C08F 263/00 525/191 |
| 2006/0251874 A1 * | 11/2006 | McClure | ............ | B01D 67/0027 428/210 |
| 2007/0073010 A1 * | 3/2007 | Pannell | ................. | C08F 210/16 526/73 |
| 2009/0241496 A1 * | 10/2009 | Pintault | .................... | C23C 4/11 55/524 |
| 2010/0119967 A1 * | 5/2010 | Inoue | ................... | G03G 9/0821 430/110.3 |
| 2010/0136473 A1 * | 6/2010 | Ishigami | ................. | G03G 9/107 430/111.35 |
| 2010/0210745 A1 * | 8/2010 | McDaniel | .............. | C09D 5/008 521/55 |
| 2012/0012528 A1 * | 1/2012 | Buekenhoudt | ..... | B01D 67/0093 210/660 |
| 2013/0189481 A1 * | 7/2013 | Grosso | ................. | B01D 67/003 428/118 |
| 2014/0030650 A1 * | 1/2014 | Komatsu | ................... | H01F 1/01 430/111.31 |
| 2014/0311967 A1 * | 10/2014 | Grossman | ................. | B32B 3/00 210/500.21 |
| 2014/0319999 A1 * | 10/2014 | Cho | ......................... | B32B 3/04 313/504 |
| 2015/0053086 A1 * | 2/2015 | Rebouillat | ................ | B32B 7/02 96/11 |
| 2015/0104364 A1 * | 4/2015 | Elomari | ............ | B01D 53/9486 423/212 |
| 2017/0149059 A1 * | 5/2017 | Dutta | .................... | H01M 4/386 |

OTHER PUBLICATIONS

Kim et al., "Palladium composite membranes using supercritical CO2 impregnation method for direct methanol fuel cells", Solid State Ionics, vol. 178, 2007, pp. 865-870.

Apr. 22, 2014 International Search Report in Patent Application PCT/IB2013/061315.

* cited by examiner

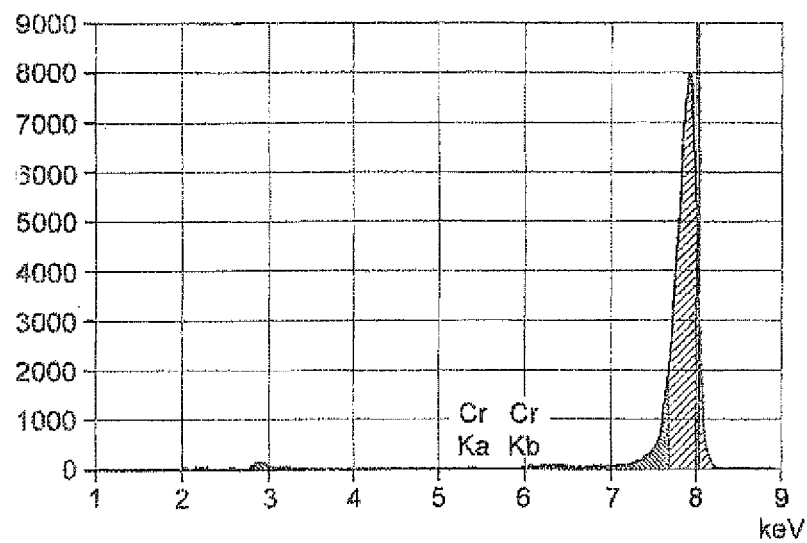
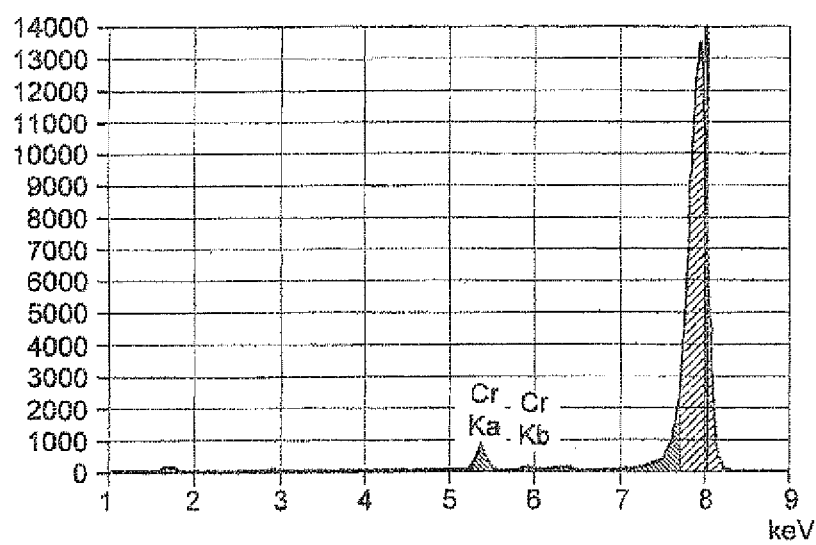

METHOD FOR PRODUCING A FILTER INTENDED TO FILTER NANOPARTICLES, OBTAINED FILTER AND ASSOCIATED METHOD FOR THE COLLECTION AND QUANTITATIVE ANALYSIS OF NANOPARTICLES

TECHNICAL FIELD

The present invention relates to the field of the collection and analysis of nanoparticles liable to be present in suspension in the air.

It relates more particularly to the preparation of a filter comprising pores which are capable of retaining, within them, nanoparticles liable to be present in an air stream intended to pass through the filter, in order to make possible the reliable surface analysis of the filter, subsequently by X fluorescence, for the quantitative analysis of the nanoparticles retained in the filter.

Finally, the invention relates to a process for the collection and analysis of associated nanoparticles.

STATE OF THE ART

The rapid expansion of nanotechnologies is making it essential to pursue studies on the health and environmental impacts of these novel materials in order to have optimum safety conditions. For some years, nanoparticles, that is to say particles of nanometric dimensions, have formed the subject of intense research and their use has begun to spread in various fields, such as health, microelectronics, energy technologies or everyday consumer products, such as paints and cosmetics. It is thus necessary to develop methods for the evaluation of the exposure to nanoparticles of workers, consumers and the environment.

The development of reliable methods for the sampling and analysis of aerosols is thus a crucial challenge in terms of public health and prevention of risks at the place of work.

Ordinarily, measurements of exposures to particles in suspension in the air are carried out by weighing filters before and after sampling. However, these gravimetric measurements are only reliable for very high amounts of particles (greater than approximately 10, indeed even approximately 100, micrograms). For the determination of smaller amounts, elemental analyses are generally carried out by sampling on the filter, followed by an analysis by microscopy or also a chemical analysis by (multi)elemental techniques, such as atomic absorption spectrometry, ICP-AES or preferably of ICP-MS type. In point of fact, this type of analysis requires a boredomsome and tedious preparation of the samples (digestion of the filter, which takes several hours, and the like).

Consequently, the applicant companies have already thought of using an X-ray fluorescence (XRF) analytical technique, in particular at low incidence, which has already proven itself, on the one hand by being extremely effective in determining the elemental composition of materials in thin layers and, on the other hand, by providing measurement results very quickly, typically in a few minutes. This X-ray fluorescence technique thus makes possible the direct analysis of a filter without a pretreatment.

Some of the inventors of the present patent application have demonstrated that, in order to be able to use this X-ray fluorescence analytical technique for the analysis of nanoparticles retained by a suitable filter, it was necessary for the latter to be as flat as possible during the analysis, and incidentally also during the collection in order to be able to directly introduce the film after the collection into an X-ray fluorescence spectrometer. Thus, a solution for rendering a filter suitable for the collection of nanoparticles as flat as possible has been described and claimed in the patent application FR 12 55785 filed on 20 Jun. 2012 on behalf of the applicant companies.

In order to be able to be quantitative, this X-ray fluorescence analytical technique additionally requires the use of an internal standard, consisting of a reference chemical element. More specifically, the use of an internal standard for an X-ray fluorescence analysis makes it possible to correct the nonlinearity of the response signal measured. For obvious reasons of nonpollution of the filtered samples, when analysis is carried out for particles initially present in an aerosol, this internal standard may not be added a posteriori to the sampling of the particles.

One solution then consists in introducing this internal standard into the filter, before the use thereof proper, that is to say before passing, over the filter, an air stream comprising the particles to be analyzed.

The usual techniques for the impregnation of filters are by dipping in a liquid solution (organic solvent, water, and the like) or by deposition of sublimation type. Neither of these techniques constitutes a process which is rapid and easy to operate on the industrial scale which can be used to impregnate a filter comprising pores for a quantitative analysis, subsequently by X-ray fluorescence, of the nanoparticles retained in the filter.

There already exist commercial filters comprising chromium salts used as reference chemical elements for analyses by epi-fluorescence microscopy. Mention may be made, among these commercial filters, of those sold by Millipore under the trade name Membrane Isopore black. However, these filters have never been used for X-ray fluorescence analysis. In addition, it is difficult to guarantee a continuous supply of these filters and it is not possible to choose a specific concentration of the internal standard.

Furthermore, various impregnation processes, in particular processes for the impregnation of metal salts, using supercritical $CO_2$ have already been described in the prior art.

The publication [1] is a review describing the incorporation of metal particles in or on substrates according to process using supercritical $CO_2$. The process described involves the dissolution of a metal precursor in supercritical $CO_2$ and then the exposure of a substrate to the solution. After incorporation of the precursor in the substrate, the precursor is reduced to its metallic form by various methods, resulting in films or in deposits of particles. The dissolution stage is carried out at different temperatures, within the range from 40 to 200° C., and under different pressures, within the range from 155 to 345 bar. The metal precursors are metal salts compressed with a ligand, which confers on them a degree of solubility in the supercritical $CO_2$, the metal of the salts being chosen solely from Pt, Pd, Ag and Ru. The substrates are of diverse structures and have different constituent materials, such as polymers chosen from Nafion®, PMP: poly(4-methylpent-1-ene); PSDB: poly(styrene-divinylbenzene); PTFE: polytetrafluoroethylene.

The publication [2] describes a method of impregnation by supercritical $CO_2$ of Nafion® membranes, with palladium salts for an application as separating membranes in fuel cells of DMFC (Direct Methanol Fuel Cell) type. The process described in this document employs Pd(II)(acetylacetonate)$_2$, which is impregnated and then reduced under its metallic form Pd(0) in a Nafion® 117 membrane, in the form of a 5×5 cm strip. The publication describes the presence and the distribution of the Pd in the membrane and also the performance of this membrane in a fuel cell. The impregnation stage is carried out for a period of time of 4 h at 80° C. and under a pressure of 200 bar of $CO_2$.

All the processes using supercritical $CO_2$ cited in the two publications above have the disadvantages of requiring a stage of reduction of the metal salts because of the application envisioned and relatively high loads of salts.

Thus, generally, none of the known techniques or processes, such as described above, constitutes a process which is rapid and easy to carry out on the industrial scale which can be used to impregnate a filter comprising pores for a quantitative analysis, subsequently by X-ray fluorescence, of the nanoparticles retained in the filter.

There thus exists a need to find a process which is rapid and easy to carry out on the industrial scale which can be used to impregnate filters comprising pores which are intended for the collection of nanoparticles, this being done in order to be able to subsequently carry out the quantitative analysis, by an X-ray fluorescence technique, of the nanoparticles collected.

Account of the Invention

In order to meet this need, a subject matter of the invention is a process for the impregnation of a filter comprising pores which are capable of retaining, within them, particles liable to be present in an air stream intended to pass through the filter, according to which the filter composed of a polymer membrane is impregnated with one or more organometallic salts by applying a treatment with supercritical $CO_2$, the metal M of each salt being chosen from the group of the rare earth metals, yttrium, scandium, chromium or a combination of these.

"Supercritical $CO_2$" is understood to mean $CO_2$ in the supercritical phase, that is to say under pressure conditions and at a temperature which are greater than those of its critical point characterized by a pressure Pc=73.8 bar and a temperature Tc=31° C.

In other words, the invention consists in doping a filter using an organometallic salt by use of supercritical $CO_2$, this being done with a very small amount of salt, without additional solvent or stage of reduction of the organometallic salt(s), the latter constituting an internal standard for a reliable quantitative analysis by X-ray fluorescence, in particular at low incidences, of the particles collected on the filter.

This is because the addition of an organometallic salt as internal standard makes it possible to correct the response measured by X-ray fluorescence (XRF) spectrometry on the "raw" spectra of the signals in order to achieve a quantitative measurement of the chemical elements collected during the sampling of particles. Without resorting to an internal calibration of the filter, it is not possible to correct the nonlinearity of the XRF response signal according to the amount of particles deposited on the filter.

The process for the impregnation of the filter according to the invention has the essential advantage of being able to be carried out on the industrial scale as it is specific, fast and easily controllable and uses very little in the way of starting materials (low volume of $CO_2$ and low amount of organometallic salts required), in contrast to the known conventional processes for the impregnation (labeling) of a filter, such as dipping in a liquid solution (organic solvent, water, and the like) or by deposition by sublimation. Furthermore, the $CO_2$ used may be recycled.

In addition, the process is reliable as it in fact makes it possible to introduce the organometallic salt into the body of the filter while retaining the properties (porosity, flatness, and the like). The metal salt is actually in a way trapped between the fibres of the constituent polymer of the filter and consequently cannot easily come out of the filter; only a subsequent additional treatment with supercritical $CO_2$ makes it possible to actually extract the organometallic salt from the filter.

According to a preferred embodiment, the treatment with supercritical $CO_2$ is carried out in an autoclave, the organometallic salt(s) being placed inside the autoclave at a distance from the filter comprising pores. It is thus possible to carry out the process according to the invention with an ordinary autoclave and without using any solvent in addition to the $CO_2$.

If appropriate, an additional solvent, of polar type, such as methanol, may be added in a small amount to the supercritical $CO_2$. This is because such an additional solvent may make it possible to increase the polarity of the $CO_2$ while retaining the supercritical phase of the mixture. It is thus possible to obtain higher molecular diffusion coefficients. The $CO_2$ preferably used in the context of the invention is of a purity greater than 99.5%. The $CO_2$ used according to the invention may be provided in a form of a liquefied gas packaged in a steel cylinder provided with a dip pipe which makes it possible to directly withdraw the liquid phase from the gas.

Preferably, the treatment with supercritical $CO_2$ consists of the following stages:

a/ purging the inside of the autoclave with $CO_2$ at ambient pressure and temperature, b/ pressurizing the inside of the autoclave to a pressure of between 73.8 and 350 bar, while maintaining the temperature at ambient temperature, c/ raising the temperature of the autoclave to a temperature between 31° C. and 150° C. over a period of time of between 20 minutes and 5 h, d/ maintaining at temperature and at pressure for a period of time of between 20 minutes and 5 hours, e/ naturally cooling the autoclave until ambient temperature is reached, f/ carrying out a calibrated escape of the $CO_2$ towards the outside of the autoclave until ambient pressure is reached.

Advantageously, a proportion by weight of the organometallic salt(s) with respect to the weight of the filter of less than or equal to 1% is selected. Thus, the relative proportion of organometallic salt(s) necessary for the process is very low, which is advantageous from the viewpoint of the cost of starting material.

The invention relates, under another of its aspects, to a filter comprising pores which are capable of retaining, within them, nanoparticles liable to be present in an air stream intended to pass through the filter, the filter being composed of a polymer membrane impregnated with one or more organometallic salts, the metal M of each salt being chosen from the group of the rare earth metals, yttrium, scandium, chromium or a combination of these.

The metal M of an organometallic salt may thus be a combination of two or more rare earth metals with one another or a combination of several rare earth metals with yttrium, scandium or chromium.

The constituent polymer of the membrane of the filter may advantageously be a polymer chosen from saturated polyesters, such as polyethylene terephthalate, polycarbonates, in particular those prepared form bisphenol A, aromatic polyethers, polysulfones, polyolefins, polyacrylates, polyamides, polyimides, and cellulose acetates and nitrates. Preferably, the filter is made of polycarbonate. Such microporous materials make it possible to achieve retention efficiencies of greater than 99.5% of nanoparticles with a diameter of between 10 and 300 nm, when the latter are in suspension in the air and when the collection flow rate is between 0.1 and 10 l·min$^{-1}$. Preferably, the filter has a thickness of between 10 and 50 μm.

Preferably, the pores of the filter are holes with a calibrated diameter of between 0.05 and 2 μm, with preferably again a density of holes of between a number of $10^5$ and $5 \times 10^8$ holes per cm$^2$. The holes may be made produced according to different known treatments, such as ion bombardment, treatments with UV radiation, chemical attacks or a combination of these different treatments.

The choice of the organometallic salt(s) is made by taking into account the chemical elements liable to be present in the nanoparticles to be withdrawn by the filter, so that there is no redundancy between them. This is because to choose an impregnation organometallic salt, the metal M of which is in addition liable to be present in the particles to be withdrawn, would prevent any XRF analysis subsequently, without the ability to distinguish the origin of the metal.

As advantageous examples, yttrium(III) tris(2,2,6,6-tetramethyl-3,5-heptanedionate) and chromium tris(2,2,6,6-tetramethyl-3,5-heptanedionate) may be used as organometallic salts according to the invention.

There are numerous ligands of the complexes of organometallic salts according to the invention which may be employed. Preferably, they confer a hydrophobic nature on the salt complex.

Thus, as alternative forms envisioned, the organometallic salt(s) may be:
  a complex of metallocene type, of formula $M(Cp)_n$, in which n is an integer between 1 and 4 and Cp is a cyclopentadiene group;
  a complex in which the metal has been subjected to chelation by groups carrying heteroelements chosen from amines and phosphines. The heteroelements are advantageously substituted by alkyl chains with at least four carbons, preferably at least partially fluorinated;
  a complex of formula $M(PR)_n$, where n is an integer between 1 and 7 and R is fluorinated substituted or branched aryl or alkyl group;
  a complex of amide type of formula $M(NR_2)_n$, where n is an integer between 1 and 4 and R is a silyl-aliphatic or aromatic group;
  a complex of phenanthroline or bathophenanthroline type of formula $M(Phe_n)_n$, where n is an integer between 1 and 4 and Phen is phenanthroline;
  a complex of carboxylate type of formula $M(OOCR)_n$, where n is an integer between 1 and 4 and R is an alkyl chain with at least four carbons, the alkyl group preferably being branched, such as —CH$_3$, CH(CH$_3$)$_2$, isobutyl, and the like;
  a complex of β-diketonate type of formula $M(RCOCH_2COR)_n$, where n is an integer between 1 and 4 and R is an alkyl chain with at least four carbons, the alkyl group preferably being branched, such as —CH$_3$, CH(CH$_3$)$_2$, isobutyl, and the like;
  a complex of alkoxide type of formula $M(OR)_n$, where R is an alkyl chain with at least four carbons, the alkyl group preferably being branched, such as —CH$_3$, CH(CH$_3$)$_2$, isobutyl, and the like;
  a complex of β-ketocarboxylate type of formula $M(OOCCH_2COR)_n$, where n is an integer between 1 and 4 and R is an alkyl chain with at least four carbons, the alkyl group preferably being branched, such as —CH$_3$, CH(CH$_3$)$_2$, isobutyl, and the like;
  a complex of phosphonate type of formula $M(O_2(O)PR)_n$, where n is an integer between 1 and 4 and R is an alkyl chain with at least four carbons, the alkyl group preferably being branched, such as —CH$_3$, CH(CH$_3$)$_2$, isobutyl, and the like;
  a complex of sulfonate type of formula $M(O_3SR)_n$, where n is an integer between 1 and 4 and R is an alkyl chain with at least four carbons, the alkyl group preferably being branched, such as —CH$_3$, CH(CH$_3$)$_2$, isobutyl, and the like.

In the alternative forms set out, the alcohol chain may advantageously be fluorinated, which promotes the dissolution of the salt in the supercritical $CO_2$.

Finally, the invention relates, under a final aspect, to a process for the collection and analysis of nanoparticles according to which the following stages are carried out:
  suction of an air stream liable to be laden with nanoparticles through a filter which has just been described;
  introduction of the filter into an X-ray fluorescence spectrometer;
  quantitative analysis by X-ray fluorescence of the nanoparticles retained by the filter by division between the fluorescence signal emitted by a chemical element of the nanoparticles and the fluorescence signal emitted by an organometallic salt impregnated into the filter.

Preferably, the flow rate for suction of the air stream through the filter is between 0.1 and 10 l·min$^{-1}$.

Preferably, prior to any collection and analysis, a filter according to the invention is fitted into a support, forming a filtration assembly as described and claimed in the patent application FR 12 55785.

DETAILED DESCRIPTION

Other advantages and characteristics will emerge more clearly on reading the detailed description, made by way of illustration and without implied limitation, with reference to the following figures, among which:

FIGS. 3A and 3B represent an X-ray fluorescence spectrum of a polycarbonate filter, respectively before and after impregnation according to the invention with a chromium salt;

Figure 1:
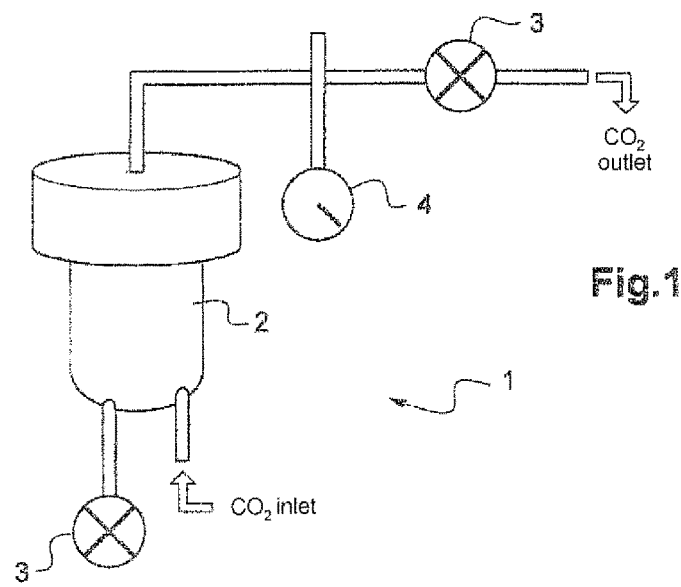
FIG. 1 is a diagrammatic view of an installation for the implementation of a process for the impregnation of a filter according to the invention.
Figures 2A, 2B:
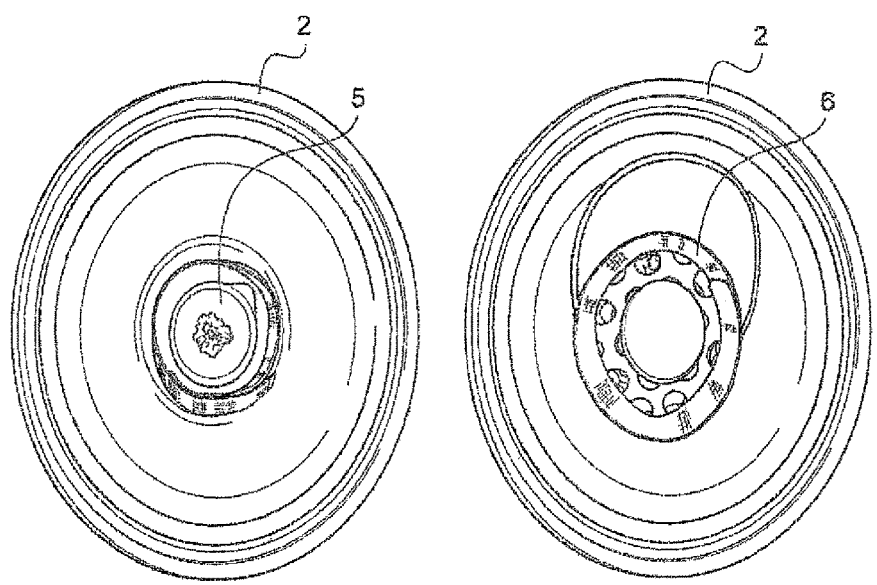
FIGS. 2A and 2B are photographic reproductions of the inside of an autoclave used in an installation according to FIG. 1, these reproductions showing devices for positioning, in the autoclave, filters and organometallic salts in accordance with the invention.
Figure 4A:
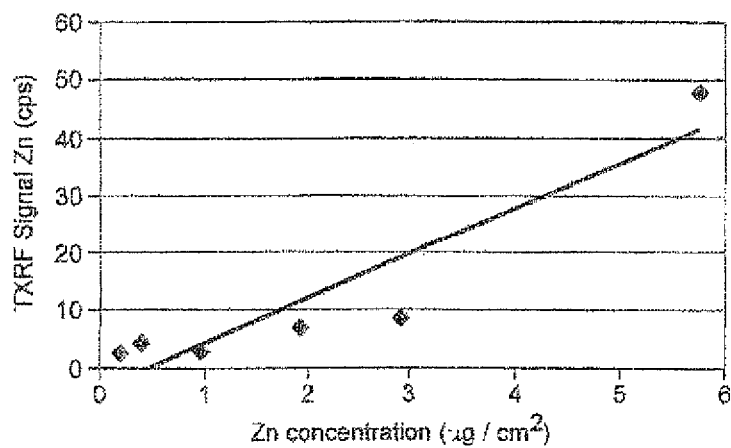
FIGS. 4A and 4B represent a measurement signal, measured by X-ray fluorescence spectrometry, of a polycarbonate filter in accordance with the invention as a function of the amounts of zinc oxide (ZnO) nanoparticles charged beforehand to the filter, according to a measurement respectively without correction and with correction by the signal of the chromium salt impregnated into the filter.
Figure 4B:
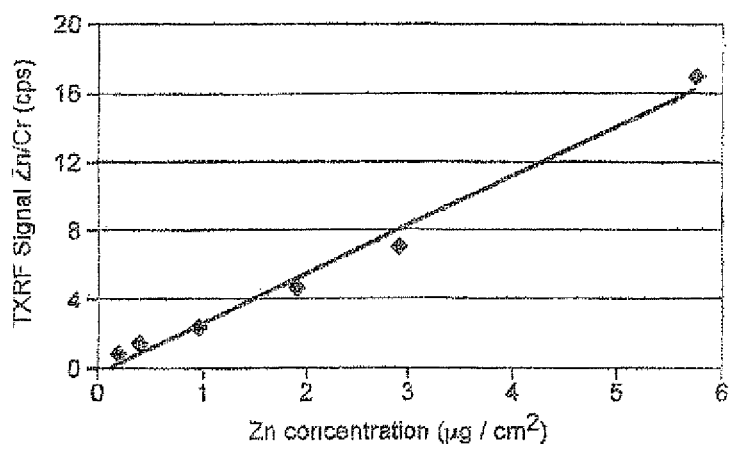
Figure 5A:
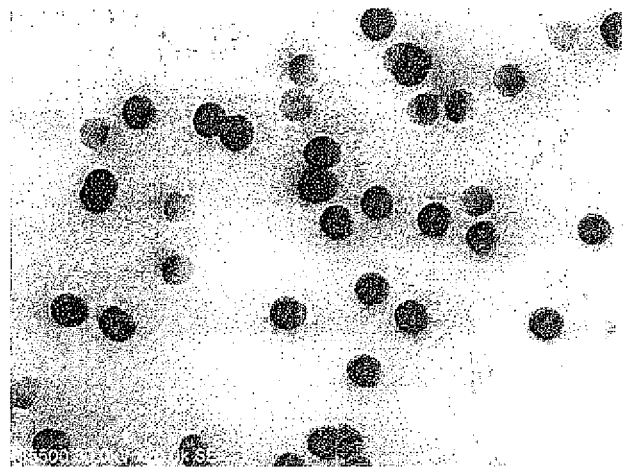
FIGS. 5A and 5B are images by scanning microscopy at the surface of a polycarbonate filter, respectively before and after impregnation according to the invention with a chromium salt.
Figure 5B:
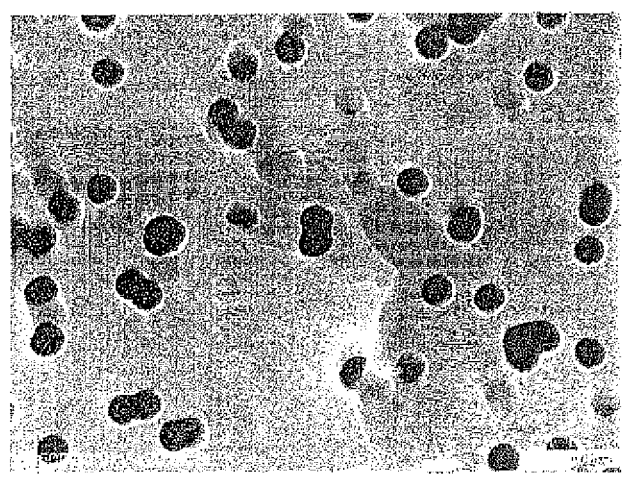

An example of a filter used to collect the nanoparticles according to the invention is a microporous membrane, made of polycarbonate, with a thickness of a few tens of microns and pierced by a multitude of holes of controlled diameter. By way of example, the holes of controlled diameter have a diameter of 0.4 μm and exhibit a density of holes of $10^5$ perforations per $cm^2$. Such a microporous filter makes it possible to achieve retention efficiencies of greater than 99.5% of the nanoparticles in suspension in the air, with a diameter of between 10 and 300 nm, with a collection flow rate of between 0.1 and 10 $l \cdot min^{-1}$.

In order to make it possible to pull such a filter flat and to keep it flat under mechanical tension, it is possible advantageously to produce a filtration assembly with a filter support in accordance with the patent application FR 12 55785.

Although not represented, such a filtration assembly is intended to be fitted into a suitable sampling cartridge in order to allow the sunctioned air stream to pass through the filter in order to carry out the collecting proper of the nanoparticles.

According to the invention, the filter is impregnated with one or more organometallic salts by applying a treatment with supercritical $CO_2$, the metal M of each salt being chosen from the group of the rare earth metals, yttrium, scandium, chromium or a combination of these.

In order to do this, the installation 1 shown diagrammatically in FIG. 1 is used: it comprises an autoclave 2, the inlet of which is connected to a $CO_2$ feed line and an outlet of which is connected to a $CO_2$ extraction line. In order to open/close, the inlet and outlet of the autoclave 2 are provided with valves 3. Finally, a manometer 4 makes it possible to monitor the pressure prevailing inside the autoclave 2.

By way of example, the autoclave has a reactor part in the form of a cylinder with an internal diameter of 50 mm and a height of 100 mm, made of stainless steel 316: it is capable of withstanding temperatures up to 150° C. and pressures ranging up to approximately 210 bar.

The valves 3 may be valves of needle gate type.

Before carrying out the impregnation proper, organometallic salts according to the invention, which have been weighed beforehand, are placed in a porcelain crucible 5 inserted at the bottom of the autoclave, as seen in FIG. 2A. By way of example, the weight of Cr salts placed in the crucible may be between 5 and 10 mg.

A pan 6 is then installed above the crucible 5, as seen in FIG. 2B.

A plurality of commercial PC filters, free from any other material, are stacked with their conditioning separators, this being done in order to avoid any direct contact between them. By way of example, the commercial PC filters may be those sold under the Isopore commercial reference by Millipore.

Thus, each filter is placed at a distance from another and also at a distance from the organometallic salts.

In other words, the organometallic salts are weighed and introduced into the crucible 5 itself at the bottom of the autoclave 2. The pan-support 6, comprising the PC filters separated from one another by conditioning separator membranes, is placed over the top, without direct contact with the salts.

The following stages are then carried out:

purging the autoclave 2 with $CO_2$, closing the outlet valve 3, pressurizing the autoclave 2 to approximately 60 bar at ambient temperature, placing the autoclave 2 under pressure in an oven, not represented, at 70° C. for a period of time of one hour: the pressure then rises to approximately 150 bar over the course of one hour, maintaining at this temperature of 70° C. and pressure of 150 bar for half an hour, removing the autoclave from the oven, naturally cooling to ambient temperature, applying a controlled escape for the decrease in pressure.

The PC filters according to the invention are then impregnated throughout their bulk with the organometallic salts.

FIGS. 3A and 3B represent the X-ray fluorescence spectra obtained before and after doping, with chromium Cr, a polycarbonate PC filter, free from any other material. A peak corresponding to the Ka re-emission line of chromium at 5.4 keV may be observed after doping.

FIGS. 4A and 4B a measurement signal, measured by X-ray fluorescence spectrometry, under grazing incidence, of a polycarbonate (PC) filter in accordance with the invention as a function of the amounts of zinc oxide (ZnO) nanoparticles charged beforehand to the filter by aerosol sampling, according to a measurement respectively without correction and with correction by the signal of the chromium salt impregnated in the filter.

Thus, the raw measurement signal of the chemical element retained in the filter, zinc Zn (FIG. 4A), is divided by that of the chromium salt impregnated in the PC filter. The corrected signal is thus linearized as a function of the concentration of the zinc (FIG. 4B). Using this straight calibrating line, it is thus possible to determine, from the signal measured, the precise amount of a sample of unknown concentration of Zn.

By way of example, if a corrected signal of 12 counts per second is measured, it is possible to quantify the prior charging density of the filter with ZnO nanoparticles equal to approximately 4.3 $\mu g/cm^2$.

It is possible to proceed thus with different chemical elements liable to occur in the form of nanoparticles in suspension in an aerosol.

Thus, the process for the impregnation of the filter with supercritical $CO_2$ according to the invention makes it possible to incorporate organometallic salts in the body of the filter in order to use their response in XRF fluorescence to calibrate the raw spectra of the chemical elements present in the particles to be collected by the filter and consequently to be able to quantify them.

In order to confirm the impact of the treatment with supercritical $CO_2$ according to the invention undergone on the polycarbonate constituting the filter, the surface condition of the latter was displayed by scanning electron microscopy (SEM), respectively before and after said treatment.

The aim of this confirmation is to ensure that the treatment with supercritical $CO_2$ according to the invention does not modify the mechanical properties of a PC filter and in particular that the size of the pores is well preserved.

FIGS. 5A and 5B respectively present the images of a fresh PC filter and of the same filter after treatment with supercritical $CO_2$ according to the invention.

A modification to the structure of the surface of the filter with a slight deterioration in flatness is observed, which is not disadvantageous to the analysis by XRF.

The size of the pores does not appear to be affected by the treatment.

This is corroborated by measurement of the pressure drop generated by the filter. Thus, when an air stream of 1 $l \cdot min^{-1}$ is passed through a PC filter, the pressure drop does not vary after treatment with supercritical $CO_2$ and remains substantially constant at approximately 50 mbar.

The invention is not limited to the examples which have just been described; it is possible in particular to combine, with one another, characteristics of the examples illustrated within alternative forms not illustrated.

REFERENCES CITED

[1]: Ying Zhang and Can Erkey, "*Preparation of supported metallic nanoparticles using supercritical fluids: a review*", J. of Supercritical Fluids, 38 (2006), 252-267.
[2]: D. Kim, J. Sauk, J. Byun, K. S. Lee and H. Kim, "*Palladium composite membranes using supercritical $CO_2$ impregnation method for direct methanol fuel cells*", Solid State Ionics, 178 (2007), 865-870.

The invention claimed is:

1. A process for the impregnation of a filter comprising pores which are capable of retaining, within them, particles liable to be present in an air stream intended to pass through the filter, according to which the filter composed of a polymer membrane is impregnated with one or more organometallic salts by applying a treatment with supercritical $CO_2$, the metal M of each salt being selected from the group consisting of lanthanum, cerium, praseodymium, neodymium, promethium, samarium, europium, gadolinium, terbium, dysprosium, holmium, erbium, thulium, ytterbium, lutetium, yttrium, scandium, chromium, and a combination of these.

2. The process for the impregnation of a filter as claimed in claim 1, according to which the treatment with supercritical $CO_2$ is carried out in an autoclave, the organometallic salt(s) being placed inside the autoclave at a distance from the filter comprising pores.

3. The process for the impregnation of a filter as claimed in claim 2, according to which the treatment with supercritical $CO_2$ consists of the following stages:
   a/ purging the inside of the autoclave with $CO_2$ at ambient pressure and temperature,
   b/ pressurizing the inside of the autoclave to a pressure of between 73.8 and 350 bar, while maintaining the temperature at ambient temperature,
   c/ raising the temperature of the autoclave to a temperature between 31° C. and 150° C. over a period of time of between 20 minutes and 5 h,
   d/ maintaining at temperature and at pressure for a period of time of between 20 minutes and 5 hours,
   e/ naturally cooling the autoclave until ambient temperature is reached,
   f/ carrying out a calibrated escape of the $CO_2$ towards the outside of the autoclave until ambient pressure is reached.

4. The process for the impregnation of a filter as claimed in claim 1, according to which a proportion by weight of the organometallic salt(s) with respect to the weight of the filter of less than or equal to 1% is selected.

5. A filter comprising pores which are capable of retaining, within them, nanoparticles liable to be present in an air stream intended to pass through the filter, the filter being composed of a polymer membrane impregnated with one or more organometallic salts, the metal M of each salt being selected from the group consisting of lanthanum, cerium, praseodymium, neodymium, promethium, samarium, europium, gadolinium, terbium, dysprosium, holmium, erbium, thulium, ytterbium, lutetium, yttrium, scandium, chromium, and a combination of these, the filter being liable to be obtained according to the process as claimed in claim 1.

6. The filter comprising pores as claimed in claim 5, the constituent polymer of the membrane being chosen from saturated polyesters.

7. The filter comprising pores as claimed in claim 6, made of polycarbonate (PC).

8. The filter comprising pores as claimed in claim 5, having a thickness of between 10 and 50 μm.

9. The filter comprising pores as claimed in claim 5, the pores of the filter being holes with a calibrated diameter of between 0.05 and 2 μm.

10. The filter comprising pores as claimed in claim 5, the density of the holes of the filter being between a number of $10^5$ and $5 \times 10^8$ holes per $cm^2$.

11. The filter comprising pores as claimed in claim 5, the organometallic salt(s) being a complex of metallocene type, of formula $M(Cp)_n$, in which n is an integer between 1 and 4 and Cp is a cyclopentadiene group.

12. The filter comprising pores as claimed in claim 5, the organometallic salt(s) being a complex in which the metal has been subjected to chelation by groups carrying heteroelements chosen from amines and phosphines.

13. The filter comprising pores as claimed in claim 12, the heteroelements being substituted by alkyl chains with at least four carbons.

14. The filter comprising pores as claimed in claim 5, the organometallic salt(s) being a complex of formula $M(PR)_n$, where n is an integer between 1 and 4 and R is a fluorinated, substituted, or branched aryl group or alkyl group.

15. The filter comprising pores as claimed in claim 5, the organometallic salt(s) being a complex of amide type of formula $M(NR_2)_n$, where n is an integer between 1 and 4 and R is a silyl-aliphatic group or an aromatic group.

16. The filter comprising pores as claimed in claim 5, the organometallic salt(s) being a complex of phenanthroline or bathophenanthroline type of formula $M(Phen)_n$, where n is an integer between 1 and 4 and Phen is phenanthroline.

17. The filter comprising pores as claimed in claim 5, the organometallic salt(s) being a complex of carboxylate type of formula $M(OOCR)_n$, where n is an integer between 1 and 4 and R is an alkyl chain with at least four carbons.

18. The filter comprising pores as claimed in claim 5, the organometallic salt(s) being a complex of β-diketonate type of formula $M(RCOCH_2COR)_n$, where n is an integer between 1 and 4 and R is an alkyl chain with at least four carbons.

19. The filter comprising pores as claimed in claim 5, the organometallic salt(s) being a complex of alkoxide type of formula $M(OR)_n$, where n is an integer between 1 and 4 and R is an alkyl chain with at least four carbons.

20. The filter comprising pores as claimed in claim 5, the organometallic salt(s) being a complex of β-ketocarboxylate type of formula $M(OOCCH_2COR)_n$, where n is an integer between 1 and 4 and R is an alkyl chain with at least four carbons.

21. The filter comprising pores as claimed in claim 5, the organometallic salt(s) being a complex of phosphonate type of formula $M(O_2(O)PR)_n$, where n is an integer between 1 and 4 and R is an alkyl chain with at least four carbons.

22. The filter comprising pores as claimed in claim 5, the organometallic salt(s) being a complex of sulfonate type of formula $M(O_3SR)_n$, where n is an integer between 1 and 4 and R is an alkyl chain with at least four carbons.

23. The filter comprising pores as claimed in claim 17, the alkyl chain being fluorinated.

24. A process for the collection and analysis of nanoparticles according to which the following stages are carried out:
   suction of an air stream liable to be laden with nanoparticles through the filter as claimed in claim 5 with an organometallic salt impregnated therein;

introduction of the filter into an X-ray fluorescence spectrometer;

quantitative analysis by X-ray fluorescence of the nanoparticles retained by the filter by division between the fluorescence signal emitted by a chemical element of the nanoparticles and the fluorescence signal emitted by the organometallic salt.

\* \* \* \* \*